United States Patent
Igarashi et al.

(10) Patent No.: US 7,326,553 B2
(45) Date of Patent: Feb. 5, 2008

(54) MALTOSE-1-PHOSPHATE-PRODUCING ENZYME

(75) Inventors: Kazuaki Igarashi, Haga-gun (JP); Shuichi Takizawa, Haga-gun (JP); Norihiko Higaki, Haga-gun (JP); Jun Hitomi, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/281,873

(22) Filed: Nov. 18, 2005

(65) Prior Publication Data

US 2006/0121576 A1 Jun. 8, 2006

Related U.S. Application Data

(63) Continuation of application No. PCT/JP2005/009501, filed on May 18, 2005.

(30) Foreign Application Priority Data

| May 18, 2004 | (JP) | ............................ 2004-148134 |
| May 18, 2004 | (JP) | ............................ 2004-148142 |
| May 18, 2004 | (JP) | ............................ 2004-148154 |

(51) Int. Cl.
- C12N 9/12 (2006.01)
- C12N 1/20 (2006.01)
- C12N 15/74 (2006.01)
- C12P 19/00 (2006.01)
- C12P 21/04 (2006.01)
- C07H 21/04 (2006.01)

(52) U.S. Cl. ...................... 435/194; 435/72; 435/69.1; 435/252.3; 435/471; 536/23.2

(58) Field of Classification Search ................ 435/194, 435/72, 69.1, 252.3, 471; 536/23.2
See application file for complete search history.

(56) References Cited

FOREIGN PATENT DOCUMENTS

WO    WO 01/00844 A2    1/2001

OTHER PUBLICATIONS

Whisstock et al. Quaterly Reviews of Biophysics, 2003, "Prediction of protein function from protein sequence and structure", 36(3): 307-340.*

N. Schilling, et al., "Maltose Phosphate in Isolated Spinach Chloroplasts", Febs Letters, vol. 61, No. 2, Jan. 1976, pp. 192-193.

A. Weinhaeusel, et al. "Application of *Escherichia coli* Maltodextrin-Phosphorylase for the Continuous Production of Glucose-1-Phosphate", Enzyme and Microbial Technology, vol. 17, Feb. 1995, pp. 140-146.

W. Erl, et al. "Monocytic Cell Adhesion to Endothelial Cells Stimulated by Oxidized Low Density Lipoprotein is Mediated by Distinct Endothelial Ligands", Atherosclerosis, 136, 1998, pp. 297-303.

J. Philip, et al., "Charge Interactions in Sperm-Egg Recognition", Acta histochem., 99, 1997, pp. 401-410.

P.E. DiCorleto, et al., "Role of Cell Surface Carbohydrate Moieties in Monocytic Cell Adhesion to Endothelium in vitro", The Journal of Immunology, vol. 143, No. 11, Dec. 1, 1989, pp. 3666-3672.

N. Schilling, "Characterization of Maltose Biosynthesis From Alpha-D-Glucose-1-Phosphate in Spinacia Oleracea. L.", Planta, 154, 1982, pp. 87-93.

B. Niehues, et al., "Isolation and Characterization of Maltokinase (ATP:Maltose 1-Phosphotransferase) From Actinoplanes Missouriensis", Arch Microbiol, vol. 180, No. 4, Oct. 2003, pp. 233-239, XP-002346641.

* cited by examiner

*Primary Examiner*—Rebecca E. Prouty
*Assistant Examiner*—Iqbal Chowdhury
(74) *Attorney, Agent, or Firm*—Oblon, Spivak, McClelland, Maier & Neustadt, P.C.

(57) ABSTRACT

The present invention provides an M-1-P-producing enzyme which employs, as starting materials, an oligosaccharide or polysaccharide having a glucose polymerization degree of 5 or more and containing an α-1,4-glycosidic bond such as maltooligosaccharide, dextrin, or starch, and which enables production of a large amount of M-1-P. The M-1-P-producing enzyme can produce M-1-P from a phosphoric acid or a salt thereof and an oligosaccharide or polysaccharide having a glucose polymerization degree of 5 or more and containing an α-1,4-glycosidic bond.

8 Claims, 2 Drawing Sheets

MALTOSE-1-PHOSPHATE-PRODUCING ENZYME

TECHNICAL FIELD

The present invention relates to a novel enzyme capable of producing maltose-1-phosphate.

BACKGROUND ART

Maltose-1-phosphate (hereinafter may be abbreviated as "M-1-P") is found in spinach chloroplast (see, for example, Non-Patent Document 1) and *Mycobacterium* cells (see, for example, Non-Patent Document 2). M-1-P has been reported to participate in inhibitory mechanism of cell adhesion (see, for example, Non-Patent Documents 3, 4, and 5), and has found utility in, for example, foods, cosmetic products, pH buffers, reagents for research, and starting materials of substrates for enzyme.

A known method for producing M-1-P employs M-1-P-producing enzyme, and specific examples thereof which have heretofore been reported include maltose kinase of *Actinoplanes missouriensis* (see, for example, Non-Patent Document 6) and maltose synthase contained in spinach (see, for example, Non-Patent Document 7). However, the former enzyme requires ATP for proceeding reaction of maltose and phosphoric acid with a substrate, and the latter requires two glucose-1-phosphate molecules for a substrate, and in consideration of high substrate cost, methods employing these enzymes are not practical in industrial production of M-1-P.

Non-Patent Document 1: FEBS Letters 1976, 61 (2): 192-3;

Non-Patent Document 2: Enzyme Microb. Technol. 1995, 17, 140-146;

Non-Patent Document 3: Atherroscleosis 1998, 136 (2): 297-303;

Non-Patent Document 4: Acta Histochem. 1997, 99 (4): 401-410;

Non-Patent Document 5: J. Immunol. 1989, 143 (11): 3666-3672;

Non-Patent Document 6: Arch Microbiol. 2003, 180 (4): 233-239;

Non-Patent Document 7: Planta. 1982, 154: 87-93.

DISCLOSURE OF THE INVENTION

The present invention provides an M-1-P-producing enzyme capable of producing M-1-P from a phosphoric acid or a salt thereof, and an oligosaccharide or polysaccharide having a glucose polymerization degree of 5 or more and containing an α-1,4-glycosidic bond.

The present invention also provides an M-1-P-producing enzyme having the following enzymatic properties.

1) Action: produces M-1-P from a phosphoric acid or a salt thereof, and an oligosaccharide or polysaccharide containing an α-1,4-glycosidic bond and having a glucose polymerization degree of 5 or more, 2) Substrate specificity: in the presence of a phosphoric acid or a salt thereof, effectively acts on an oligosaccharide or polysaccharide having a glucose polymerization degree of 6 or more and containing an α-1,4-glycosidic bond or a degraded product of the oligosaccharide or polysaccharide to thereby produce M-1-P; weakly acts on an oligosaccharide having a glucose polymerization degree of 5; and exhibits substantially no action on an oligosaccharide having a degree of polymerization of 2 to 4, 3) Molecular weight: approximately 75 kDa (SDS-PAGE), 4) Optimum pH: 6.5 to 8.0, 5) Optimum temperature: 35 to 50° C.

The present invention also provides proteins defined by the following (a), (b), (c), or (d), and genes encoding the proteins.

(a) A protein having an amino acid sequence represented by SEQ ID NO: 2, (b) A protein having an amino acid sequence of (a), in which one to several amino acid residues are deleted, substituted, or added, the protein being capable of producing M-1-P, (c) A protein having an amino acid sequence exhibiting 60% or more homology with that of (a), the protein being capable of producing M-1-P, (d) A protein which has an amino acid sequence exhibiting 38% or more homology with that of (a), the protein being capable of producing M-1-P, and contains an amino acid sequence represented by Ala-Glu-Asn-Pro-Pro-Lys-Lys(or Arg)-Tyr-Gln(or Glu)-Asp-Ile (SEQ ID NO: 11) or Phe-Arg-Val(or Ile)-Asp-Asn-Pro-His-Thr-Lys-Pro (SEQ ID NO: 12).

The present invention also provides a maltose-1-phosphate-producing enzyme gene having DNA of the following (a), (b), or (c).

(a) A DNA which has a nucleotide sequence represented by SEQ ID NO: 1, (b) A DNA which is capable of hybridizing a DNA having the nucleotide sequence of (a) under stringent conditions and which encodes a protein capable of producing M-1-P, (c) A DNA which has a nucleotide sequence exhibiting 60% or more homology with the nucleotide sequence of (a) and which encodes a protein capable of producing M-1-P.

The present invention also provides a recombinant vector harboring the gene. The present invention also provides a transformant containing the recombinant vector.

The present invention also provides a method for producing an M-1-P-producing enzyme, characterized by culturing a microorganism capable of producing the enzyme or the protein in a medium containing 50 mM or more of a phosphoric acid or a salt thereof, and collecting the M-1-P-producing enzyme produced in the medium.

The present invention also provides a medium for producing the enzyme or the protein, wherein the concentration of the phosphoric acid or a salt thereof is 50 mM or more.

The present invention also provides a method for producing M-1-P, characterized by causing the enzyme or the protein to act on a phosphoric acid or a salt thereof, and an oligosaccharide or polysaccharide containing an α-1,4-glycosidic bond and having a glucose polymerization degree of 5 or more.

The present invention also provides a method for producing M-1-P, characterized by culturing a microorganism capable of producing the enzyme or the protein in a medium containing 1 mM or more of a phosphoric acid or a salt thereof and an oligosaccharide or polysaccharide which contains an α-1,4-glycosidic bond and has a glucose polymerization degree of 5 or more, and collecting M-1-P produced and accumulated in the medium.

BEST MODES FOR CARRYING OUT THE INVENTION

The present invention relates to provision of an M-1-P-producing enzyme capable of producing a large amount of M-1-P through use of, as a starting material, an oligosaccharide or polysaccharide containing an α-1,4-glycosidic bond and having a glucose polymerization degree of 5 or more. The present invention also relates to a method for producing an M-1-P-producing enzyme capable of producing a large amount of M-1-P through use of the oligosaccharide or polysaccharide as a starting material. The present invention further relates to a method for producing M-1-P, the method enabling, at low cost, production of a large amount of M-1-P through use of the oligosaccharide or polysaccharide as a starting material.

The present inventors have searched for natural microorganisms and enzymes which can produce M-1-P in a medium, and, as a result, have discovered a novel M-1-P-producing enzyme capable of producing M-1-P from a phosphoric acid or a salt thereof and an oligosaccharide or polysaccharide having a glucose polymerization degree of 5 or more and containing an α-1,4-glycosidic bond. The present inventors have also found that, by culturing a microorganism capable of producing the enzyme in a phosphate-rich medium, the enzyme is produced in the supernatant of the culture broth at high yield. The present inventors have also found that, by culturing a bacterium belonging to the family *Corynebacterium* in the presence of a sugar and a phosphoric acid or a salt thereof at high concentration, highly concentrated M-1-P is directly obtained in the medium in a large amount.

Use of the M-1-P-producing enzyme of the present invention (hereinafter may be referred to as "the enzyme of the present invention") enables production of a large amount of M-1-P with ease, employing as a substrate an inexpensive oligosaccharide or polysaccharide containing an α-1,4-glycosidic bond. According to the present invention, an M-1-P-producing enzyme can be produced in an effective and convenient manner, through a very simple process including culturing a microorganism, separating the culture broth supernatant (removal of cells), and purification. According to the method of the present invention, M-1-P can be produced directly in a medium at high concentration, enabling production of a large amount of M-1-P at low cost and without cumbersome processes.

The enzyme of the present invention may be prepared by, for example, culturing a microorganism capable of producing the M-1-P-producing enzyme of the present invention in a medium containing a sugar, preferably an oligosaccharide or polysaccharide having a glucose polymerization degree of 5 or more and containing an α-1,4-glycosidic bond, and collecting the enzyme from the cultured product. Alternatively, the enzyme of the present invention may be prepared by artificially expressing a gene encoding the enzyme of the present invention, thereby producing a polypeptide having M-1-P-producing enzyme activity, and collecting the same.

Examples of the microorganism capable of producing the enzyme of the present invention include bacteria belonging to the family *Corynebacterium* such as *Corynebacterium* sp. JCM1300, *Corynebacterium flavescens*, *Corynebacterium glutamicum*, *Corynebacterium hoagii*, *Corynebacterium vitaeruminis*, *Corynebacterium pilosum*, *Corynebacterium amycolatum*, *Corynebacterium matruchoti*, *Corynebacterium minutissimum*, *Corynebacterium striatum*, and *Corynebacterium callunae*. Of these, *Corynebacterium* sp. JCM1300, *Corynebacterium flavescens* JCM1317, *Corynebacterium glutamicum* JCM1318, *Corynebacterium hoagii* JCM1319, *Corynebacterium glutamicum* JCM1321, *Corynebacterium vitaeruminis* JCM1323, *Corynebacterium pilosum* JCM3714, *Corynebacterium amycolatum* JCM7447, *Corynebacterium matruchotii* JCM9386, *Corynebacterium minutissimum* JCM9387, *Corynebacterium striatum* JCM9390, and *Corynebacterium callunae* IFO15359 are preferred. From the viewpoint of high M-1-P productivity, *Corynebacterium* sp. JCM1300, *Corynebacterium hoagii* JCM1319, *Corynebacterium glutamicum* JCM1321, and *Corynebacterium callunae* IFO15359 are particularly preferred. Alternatively, there may be employed a transformant, described below, containing a recombinant vector containing a gene of the enzyme of the present invention.

Examples of sugar (carbon source) incorporated into the medium includes monosaccharide, disaccharide, oligosaccharide, and polysaccharide. The sugars may be employed in combination of two or more species. Of these, preferred species include an oligosaccharide or polysaccharide having a glucose polymerization degree of 5 or more and containing an α-1,4-glycosidic bond. Examples of the oligosaccharide or polysaccharide having a glucose polymerization degree of 5 or more and containing an α-1,4-glycosidic bond include starch, amylose, dextrin, maltose, maltooligosaccharide, amylopectin, glycogen, and starch-degraded products. Among them, starch, dextrin, and maltooligosaccharide, which are inexpensive, are preferred. These sugars may be employed in combination of two or more species. The concentration of the oligosaccharide or polysaccharide in the medium is preferably 1 to 70 mass %, more preferably 10 to 70 mass %, still more preferably 20 to 50 mass %, from the viewpoint of effectiveness.

The above-described culture is preferably performed in a medium further containing a phosphoric acid or a salt thereof. The concentration of a phosphoric acid or a salt thereof is typically 50 mM or more, preferably 50 mM to 2,000 mM, more preferably 100 mM to 1,200 mM, still more preferably 400 to 1,000 mM. When the amount of a phosphoric acid or a salt falls within the above range, an M-1-P-producing enzyme can be effectively produced and accumulated in the culture broth supernatant. Examples of the phosphoric acid or a salt thereof include phosphoric acid, metaphosphoric acid, tripolyphosphoric acid, polyphosphoric acid, diphosphoric acid, polymetaphosphoric acid, and the salt thereof, and examples of the salt include a sodium salt and a potassium salt. Preferred examples of the phosphoric acid salt include monopotassium phosphate, dipotassium phosphate, monosodium phosphate, and disodium phosphate.

No particular limitations are imposed on the medium employed in the present invention, so long as the medium allows growth of a bacterium capable of producing an M-1-P-producing enzyme. There may be employed a liquid medium containing, in addition to the above sugar or polysaccharide, a carbon source other than saccharide, a nitrogen source, metallic minerals, or vitamins. Examples of the carbon source other than sugar include organic acid salts such as acetic acid salts. Examples of the nitrogen source include ammonia; inorganic and organic ammonium salts such as ammonium chloride, ammonium sulfate, ammonium nitrate, ammonium carbonate, ammonium phosphate, and ammonium acetate; nitrogen-containing organic substances such as urea, peptone, meat extract, yeast extract, and casein-hydrolyzed products; and amino acids such as glycine, glutamic acid, alanine, and methionine. Examples of the metallic minerals include sodium chloride, ferrous sulfate, magnesium sulfate, manganese sulfate, zinc sulfate, and calcium carbonate. These compounds may be employed singly or in combination of two or more species in accordance with needs.

The culture is performed under pH and temperature conditions which are appropriately adjusted so that the microorganism can be grown sufficiently. The culture may be performed through shaking culture, anaerobic culture, stationary culture, or culture in a fermentation tank. Alternatively, resting cell reaction or immobilized cell reaction may be employed.

Collection of the M-1-P-producing enzyme from the cultured product may be performed through a known method. For example, if necessary, the cultured product is pretreated to bacteriolysis through treatment with ultrasound or with surfactant, the cultured product is subjected to separate and remove the cells through centrifugation or filtration. And the supernatant is subjected to ultrafiltration, salting out, solvent precipitation, ion exchange, hydrophobic chromatography, gel filtration, drying, or a similar process, or a combination of such processes, to thereby concentrate the enzyme.

In these steps, the enzyme is caused to precipitate through salting out employing, for example, ammonium sulfate or through solvent precipitation employing, for example, cold acetone. Subsequently, the precipitated product is subjected to centrifugation or desalting. Thus, a freeze-dried powder or spray-dried powder can be obtained. In the desalting step, dialysis, gel filtration through use of, for example, Sephadex G-10 (Pharmacia Biotech), ultrafiltration, or a similar process is employed. The thus-obtained enzyme solution or dried powder may be employed without further treatment, or may further be subjected to crystallization or granulation through a known method.

As described above, when culture is performed in a medium containing a phosphoric acid or a salt thereof at high concentration, the enzyme of the present invention is extracellularly produced, and can readily be obtained through collection from the cultured product. In addition, since the enzyme of the present invention is extracellularly produced, an immobilized enzyme can be produced without cumbersome processes.

Thus, according to the method of the present invention employing a phosphoric acid or a salt thereof at high concentration, the M-1-P-producing enzyme can be produced outside the cells directly, and can thus be obtained without intricate processes such as cell pulverization. In addition, the medium is merely supplemented with a phosphoric acid, which is a compound having a low molecular weight, burden to the purification steps are considerably reduced, and a high-purity product of the enzyme can readily be prepared.

According to the method, no special treatment is needed to produce M-1-P in the culture broth. In addition, a glycoside can be obtained with no special procedure, by directly causing reaction of a compound serving as an aglycon with M-1-P in the culture broth.

The thus-produced enzyme of the present invention is a novel M-1-P-producing enzyme which is capable of producing M-1-P from a phosphoric acid or a salt thereof and an oligosaccharide or polysaccharide having a glucose polymerization degree of 5 or more and containing an $\alpha$-1,4-glycosidic bond. The enzymatic properties of the enzyme will next be described. Measurement of the enzyme activity was performed through use of, as substrates, 2% dextrin MAX 1000 (Matsutani Chemical) and 1M phosphate buffer (pH 7) in the following manner: a suitably diluted enzyme was added to the substrates, the mixture was incubated for 1 hour at 37° C., and the produced M-1-P was quantified through HPLC (see Example 1).

1) Action

The enzyme of the present invention produces M-1-P from a phosphoric acid or a salt thereof, and an oligosaccharide or polysaccharide having a glucose polymerization degree of 5 or more and containing an $\alpha$-1,4-glycosidic bond.

The enzyme of the present invention exhibits phosphorylase activity; i.e., the enzyme acts, in the presence of a phosphoric acid or a salt thereof, on an oligosaccharide or polysaccharide having a glucose polymerization degree of 5 or more and containing an $\alpha$-1,4-glycosidic bond, and recognizes a maltose unit thereof, to thereby catalyze phosphorolysis of the oligosaccharide or polysaccharide. No phosphorylase has been reported, except for a phosphorylase which recognizes glucose or other monosaccharides to thereby produce glucose-1-phosphate or other products, and nothing has been known in relation to an enzyme which recognizes disaccharide to produce disaccharide phosphate.

In the absence of a phosphoric acid, the enzyme of the present invention acts on a maltooligosaccharide and transfers per unit of maltose. That is, when the enzyme of the present invention acts on maltohexaose (DP=6), a maltooligosaccharide (DP=4, DP=6, DP=8, DP=10, etc.) is produced, and when the enzyme of the present invention acts on maltoheptaose (DP=7), maltooligosaccharide (DP=5, DP=7, DP=9, DP=11, etc.) is produced. Thus, the enzyme of the present invention has activity of acting on maltopentaose or higher oligosaccharide to cause maltose-unit transfer. Although a maltosyltransferase has already been reported in Eur. J. Biochem. (1998) 250, 1050-1058, no report describes that the maltosyltransferase produces M-1-P. Moreover, the existing maltosyltransferase acts on maltotriose (DP=3) or other low molecules, and, when the existing maltosyltransferase is caused to act on an oligosaccharide of DP=3 or higher, a low-polymerized oligosaccharide of DP=1 to 3 having a low molecular weight is produced. On the contrary, the enzyme of the present invention exhibits substantially no action on maltooligosaccharide of DP=3 or 4, and weakly acts on maltooligosaccharide of DP=5. In addition, even when the enzyme of the present invention acts on maltooligosaccharide of DP=5 or higher, substantially no oligosaccharide of low polymerization degree (DP=1 to 3) is produced. Therefore, the enzyme of the present invention is different from the existing maltosyltransferase.

Thus, the enzyme of the present invention is a novel enzyme having both phosphorylase activity (i.e., capable of acting on an oligosaccharide or polysaccharide having a glucose polymerization degree of 5 or more and containing an $\alpha$-1,4-glycosidic bond and recognizing a maltose unit to thereby cause phosphorolysis of the oligosaccharide or polysaccharide) and maltose transfer activity (i.e., capable of extending by unit of maltose). Therefore, the enzyme of the present invention may be named, for example, maltodextrin·maltosylphosphorylase, maltodextrin: orthophosphoric acid-$\alpha$-1-maltosyltransferase, or maltosyltransferase.

Examples of the oligosaccharide or polysaccharide having a glucose polymerization degree of 5 or more and containing an α-1,4-glycosidic bond (i.e., a substrate of the enzyme of the present invention) include starch, amylose, dextrin, maltose, maltooligosaccharide, amylopectin, glycogen, and starch-degraded products.

Examples of the phosphoric acid or a salt thereof include phosphoric acid, metaphosphoric acid, tripolyphosphoric acid, polyphosphoric acid, diphosphoric acid, polymetaphosphoric acid, and a salt thereof. The salt is preferably a sodium salt or potassium salt. Particularly preferred examples of the phosphoric acid salt include monopotassium phosphate, dipotassium phosphate, monosodium phosphate, and disodium phosphate.

No particular limitations are imposed on the concentration of the substrates. However, the concentration of a phosphoric acid or a salt thereof is preferably 50 mM to 2,000 mM, more preferably 100 mM to 1,200 mM, even more preferably 400 to 1,000 mM. The concentration of the oligosaccharide or polysaccharide having a glucose polymerization degree of 5 or more and containing an α-1,4-glycosidic bond is preferably 1 to 70 mass %.

2) Substrate Specificity

The enzyme of the present invention effectively acts on, in the presence of a phosphoric acid or a salt thereof, an oligosaccharide or polysaccharide having a glucose polymerization degree of 6 or more and containing an α-1,4-glucosidic bond or a degraded product of the oligosaccharide or polysaccharide to thereby produce M-1-P. The enzyme of the present invention weakly acts on an oligosaccharide having a glucose polymerization degree of 5, and exhibits substantially no action on an oligosaccharide having a polymerization degree of 2 to 4. Examples of the polysaccharide include amylose, amylopectin, glycogen, dextrin, and starch.

3) Molecular Weight

The enzyme of the present invention has a molecular weight of about 75 kDa as measured through sodium dodecyl sulfate-polyacrylamide gel electrophoresis (SDS-PAGE) (it should be noted that, when SDS-PAGE is employed, measurement data may fluctuate by ±5 kDa or thereabouts, depending on the SDS-PAGE conditions).

4) Optimum pH and Active pH

As substrates, 2% maltoheptaose (G7: Seikagaku Corporation) and 700 mM phosphate buffers at every pH from 5.5 to 8.5 are employed. The purified enzyme is added to the substrates so as to attain a concentration of 0.28 U/mL (see Example 1), and the mixture is allowed to react for 1 hour at 37° C., followed by measurement of enzyme activity. The enzyme of the present invention exhibits an optimum pH ranging from about 6.5 to about 8.0. In this range, the enzyme exhibits 80% or more of the activity measured at pH 7.5 (the maximum activity). At a pH of 5.5 to 8.5, the enzyme exhibits 50% or more of the activity measured at pH 7.5.

5) Optimum Temperature and Active Temperature

As substrates, 1M potassium phosphate buffer (pH 7) and 2% maltoheptaose (G7: Seikagaku Corporation) are employed. The purified enzyme is added to the substrate so as to attain a concentration of 0.168 U/mL, and the mixture is allowed to react for 1 hour at a temperature of 30° C. to 70° C. The reaction mixture is treated for 10 minutes at 95° C. for deactivation of the enzyme. The reaction mixture is diluted 101-fold, followed by measurement of enzyme activity. The enzyme of the present invention exhibits an optimum temperature of 35 to 50° C. In this range, the enzyme exhibits 80% or more of the activity measured at 40° C. (the maximum activity). At a temperature of 30° C. to 55° C., the enzyme exhibits 30% or more of the activity measured at 40° C.

Next will be described the protein of the present invention and a gene encoding the protein.

The protein of the present invention is capable of producing M-1-P, as described above, and defined by the following (a), (b), (c), or (d);

(a) A protein having an amino acid sequence represented by SEQ ID NO: 2, (b) A protein having an amino acid sequence of (a), in which one to several amino acid residues are deleted, substituted, or added, and being capable of producing M-1-P, (c) A protein having an amino acid sequence exhibiting 60% or more homology with that of (a), and being capable of producing a M-1-P, and (d) A protein having an amino acid sequence exhibiting 38% or more homology with that of (a), being capable of producing a maltose-1-phosphate, and containing an amino acid sequence represented by Ala-Glu-Asn-Pro-Pro-Lys-Lys(or Arg)-Tyr-Gln(or Glu)-Asp-Ile (SEQ ID NO: 11) or Phe-Arg-Val(or Ile)-Asp-Asn-Pro-His-Thr-Lys-Pro (SEQ ID NO: 12).

Deletion, substitution, or addition of one to several amino acid residues in the amino acid sequence represented by SEQ ID NO: 2 is preferably a deletion, substitution, or addition of one to ten amino acid residues, the addition including addition of one to several amino acid residues to each end of the sequence. A nucleotide sequence encoding the amino acid sequence may be obtained from the natural world, and may also be prepared further through site-directed mutagenesis or other techniques known per se. For example, the nucleotide sequence may be obtained by introducing a mutation by means of, for example, a mutation-introducing kit employing site-directed mutagenesis [Mutan-super Express Km kit (Takara)].

The protein of the present invention encompasses a protein which is capable of producing M-1-P and which exhibits 60% or more homology with the amino acid sequence represented by SEQ ID NO: 2 as determined when the amino acid sequence of SEQ ID NO: 2 is appropriately aligned with a corresponding region of the amino acid sequence of the protein. The homology of the region is preferably 70% or more, more preferably 80% or more, still more preferably 90% or more.

The 675 amino acid residues represented by SEQ ID NO: 2 were subjected to BLASTP homology search of the NCBI database, which revealed that the sequence exhibits 99% to 38% homology with proteins originating from microorganisms such as *Corynebacterium glutamicum* ATCC13032 (99%), *Corynebacterium efficiens* YS-314 (84%), *Corynebacteriumd iphtheriae* (66%), and *Mycobacterium smegmatis* (60%) (see Example 7). These proteins are classified into the Family 13 of Glycosyl Hydrolase in the saccharide-related enzyme database CAZy, and deduced to be glycosidase, amylase, glucanase, or the like. However, the deduction is merely based on the genomic sequence of these proteins. Genes of the proteins have never been isolated, and expression of the genes to produce the proteins has never been examined. Thus, nothing has been known in relation to the function. Comparison of the amino acid sequences in terms of the alignment reveals highly conserved regions of the 342nd to 352nd amino acid residues (Ala-Glu-Asn-Pro- Pro-Lys-Lys(or Arg)-Tyr-Gln(or Glu)-Asp-Ile) [see the 342nd to 352nd of SEQ ID NO: 2; SEQ ID NO: 11] and the 383rd to 392nd amino acid residues (Phe-Arg-Val(or Ile)-Asp-Asn-Pro-His-Thr-Lys-Pro) [see the 383rd to 392nd of SEQ ID NO: 2; SEQ ID NO: 12] from the N-terminus of the amino acid sequence of the M-1-P-producing enzyme of the present invention.

Therefore, the protein of the present invention includes, as preferred examples, proteins which exhibit 38% or more, more preferably 80% or more, still more preferably 90% or more, further more preferably 95% or more homology with SEQ ID NO: 2, which is capable of producing M-1-P, and which contains an amino acid sequence represented by Ala-Glu-Asn-Pro-Pro-Lys-Lys(or Arg)-Tyr-Gln(or Glu)-Asp-Ile (SEQ ID NO: 11) and/or Phe-Arg-Val(or Ile)-Asp-Asn-Pro-His-Thr-Lys-Pro (SEQ ID NO: 12).

No particular limitations are imposed on the gene of the M-1-P-producing enzyme of the present invention, so long as the gene encodes any of the above proteins. However, preferred are genes containing a nucleotide sequence represented by SEQ ID NO: 1 and genes containing DNA which are capable of hybridizing with a DNA fragment having a nucleotide sequence represented by SEQ ID NO: 1 under stringent conditions.

Examples of the "under stringent conditions" include a condition described in Molecular cloning—a Laboratory Manual, 2nd edition (Sambrook et al., 1989). For example, hybridization is performed by adding a DNA fragment and a probe to a solution containing 100 mg/mL of herring sperm DNA and 6×SSC (composition of 1×SSC; 0.15M sodium chloride, 0.015M sodium citrate, pH 7.0), 0.5% SDS, and 5× Denhart, and incubating the mixture for 8 to 16 hours at 65° C.

The enzyme gene of the present invention encompasses a DNA which exhibits 60% or more homology with the nucleotide sequence represented by SEQ ID NO: 1 and which encodes a protein capable of producing M-1-P. The homology of the sequence is preferably 70% or more, more preferably 80% or more, still more preferably 90% or more, further more preferably 95% or more.

The homology of the amino acid sequence or the nucleotide sequence is calculated through the Lipman-Pearson method (Science, 227, 1435, (1985)). Specifically, analysis is performed through use of a homology analysis (Search homology) program of genetic information processing software Genetyx-Win (Ver.5.1.1; Software Development Co., Ltd.) (Unit size to compare (ktup)=1).

The enzyme gene of the present invention may be obtained by examining chromosomal DNA of the enzyme-producing microorganism employed in the present invention (such as microorganisms belonging to the family *Corynebacterium* as mentioned above) through a typical DNA cloning technique based on the DNA nucleotide sequence or the amino acid sequence according to the present invention. The examination of chromosomal DNA may be performed through hybridization employing a library, PCR employing the chromosomal DNA as a template, or a modified method of these techniques.

A recombinant vector containing the enzyme gene of the present invention may be prepared by introducing the enzyme gene into a vector which can be replicated and maintained in a host cell, which allows stable expression of the enzyme, and which can stably maintain the gene. Examples of the vector employable when *Escherichia coli* is used as a host include pUC18, pBR322, and pHY300PLK. Examples of the vector employable when *Bacillus subtilis* is used as a host include pUB110pHSP64 (Sumitomo et al., Biosci. Biotechnol. Biocem., 59, 2172-2175, 1995), and pHY300PLK (Takara Bio Inc.)

Expression of the enzyme gene of the present invention is preferably performed by transferring the enzyme gene of the present invention to a host cell to thereby prepare a transformant, seeding the transformant in a medium containing an assimilable carbon source, an assimilable nitrogen source, and other essential nutrients, and culturing through a routine method. The transformant may be obtained by ligating the enzyme gene of the present invention to an autonomously replicable vector to thereby prepare a recombinant DNA, and introducing the recombinant DNA into a host microorganism which is suitable for expression of the DNA. No particular limitations are imposed on the host bacterium, and examples include Gram-positive bacteria such as bacteria belonging to the family *Bacillus* (*Bacillus subtilis*), Gram-negative bacteria such as *Escherichia coli*, and fungi such as those belonging to the family *Streptomyces* (actinomycetes), the family *Saccharomyces* (yeast), or the family *Aspergillus* (molds). Collection and purification of the enzyme contained in the culture broth may be performed through a routine method, and the thus-obtained enzyme may be further subjected to lyophilization, spray-drying, or crystallization in accordance with needs.

M-1-P can be produced in a large amount through use of the thus-produced enzyme of the present invention at low cost. Specifically, the enzyme of the present invention is added to a solution containing the substrates; i.e., a phosphoric acid or a salt thereof and an oligosaccharide or polysaccharide having a glucose polymerization degree of 5 or more and containing an α-1,4-glycosidic bond, to thereby cause reaction of the enzyme with the substrate. Alternatively, the enzyme of the present invention is caused to react with the substrates through an immobilized enzyme method; i.e., the enzyme of the present invention is immobilized to a carrier, and the substrates are caused to flow through a column containing the carrier. No particular limitations are imposed on the carrier to which the enzyme is immobilized, so long as the carrier is commonly used. For example, an ion exchange resin or a synthetic absorption resin may be employed.

Alternatively, M-1-P can be obtained by culturing any of the above-mentioned microorganisms which are capable of producing the enzyme of the present invention in a medium containing a sugar and a phosphoric acid or a salt thereof, to thereby yield M-1-P in the culture broth.

Preferred examples of the sugar incorporated into the medium include monosaccharide, disaccharide, oligosaccharide, and polysaccharide which contain glucose as a structural sugar. Among them, more preferred is an oligosaccharide or polysaccharide containing an α-1,4-glycosidic bond, such as starch, amylose, dextrin, maltose, maltooligosaccharide, amylopectin, glycogen, or a starch-degraded product. Of these, starch, dextrin, and maltooligosaccharide, which are inexpensive, are preferred. These sugars may be employed in combination with two or more species.

Concentration of sugar in the medium is preferably 1 to 70 mass %, more preferably 10 to 70 mass %, even more preferably 20 to 50 mass %, from the viewpoint of effectiveness.

Examples of the phosphoric acid or a salt thereof incorporated into the medium include phosphoric acid, metaphosphoric acid, tripolyphosphoric acid, polyphosphoric acid, diphosphoric acid, polymetaphosphoric acid, and salts thereof. The salt is preferably a sodium salt or a potassium salt. Preferred examples of the phosphoric acid salt include monopotassium phosphate, dipotassium phosphate, monosodium phosphate, and disodium phosphate. In the present invention, a phosphoric acid or a salt thereof, or a mixture of a plurality of phosphoric acid salts is preferably employed.

From the viewpoint of effectiveness, the concentration of a phosphoric acid or a salt thereof in the medium is 1 mM or more, and is preferably 1 mM to 2 M, more preferably 50 mM to 1 M.

No particular limitations are imposed on the medium employed, so long as the medium allows growth of a microorganism capable of producing the enzyme of the present invention, and there may be employed, for example, a liquid medium containing, in addition to a sugar and a phosphoric acid or a salt thereof described above, a carbon source, a nitrogen source, metallic minerals, vitamins, etc.

Examples of the carbon source other than sugar include organic acid salts such as acetic acid salts. Examples of the nitrogen source include ammonia; inorganic and organic ammonium salts such as ammonium chloride, ammonium sulfate, ammonium nitrate, ammonium carbonate, ammonium phosphate, and ammonium acetate; nitrogen-containing organic compounds such as urea, peptone, meat extract, yeast extract, and casein-hydrolyzed products; and amino acids such as glycine, glutamic acid, alanine, and methionine. Examples of the metallic minerals include sodium chloride, ferrous sulfate, magnesium sulfate, manganese sulfate, zinc sulfate, and calcium carbonate. These compounds may be employed singly or in combination of two or more species in accordance with needs.

The culture is performed under pH and temperature conditions which are appropriately adjusted so that the microorganism can be grown sufficiently. Typically, the culture is preferably performed for 12 hours to 96 hours at a pH of 4 to 8 and a temperature of 25° C. to 40° C. The culture may be performed through stationary culture, shaking culture, or culture in a fermentation tank. In addition, resting cell reaction and immobilized cell reaction may be employed.

Collection of M-1-P contained in the cultured product may be performed through a method known per se. According to the method of the present invention, there may be produced, in addition to M-1-P, glucose-1-phosphate or other phosphorylated saccharides. Therefore, after the cells are separated and removed, M-1-P is preferably isolated through, for example, ultrafiltration, reverse osmosis membrane, electrodialysis, ion exchange membrane, ion exchange resin, active carbon, or treatment with a synthetic absorbent, and subsequently through crystallization or salting out, in accordance with needs. The thus-obtained M-1-P may be further purified through ion exchange chromatography or other techniques, in accordance with needs.

As mentioned above, the enzyme which catalyzes production of M-1-P in the method of the present invention for producing M-1-P is a novel enzyme. Therefore, when there is employed a bacterium cell in which a gene region encoding an enzyme that catalyzes production of glucose-1-phosphate or other phosphorylated saccharides is deactivated or eliminated from the genome, M-1-P of interest can be selectively obtained. In particular, bacterium belonging to the family Corynebacterium in which a gene encoding extracellular maltodextrin phosphorylase is deactivated is preferably used. The elimination or deactivation of a gene of interest may be performed through a known method (e.g., Mol. Gen. Genet., 223, 268, 1990).

EXAMPLES

Example 1

Method for Determining Activity of M-1-P-Producing Enzyme

Activity of an M-1-P-producing enzyme was determined through the following procedure.

As substrates, 2% dextrin MAX 1000 (Matsutani Chemical) and 1M phosphate buffer (pH 7) were employed. To the substrates, a suitably diluted enzyme was added, and the mixture was incubated for one hour at 37° C., followed by quantification of the produced M-1-P through HPLC. Specifically, quantification of M-1-P was performed through use of a DX500 chromatography system (product of DIONEX Corporation) (column: CarboPac PA1 (4×250 mm), detector: ED40 pulsed amperometric detector, eluent: (solution A) 100 mM sodium hydroxide; (solution B) 100 mM sodium hydroxide containing 1M sodium acetate). Linear gradient analysis was employed (initial concentration: solution A 90%: solution B 10%, 0-17 min.: solution A 18.5%: solution B 81.5%). As standard substances, 100 mM and 50 mM M-1-P products (product of SIGMA) were employed. A peak was observed at about 15.5 minutes. One enzyme unit (1 U) is defined as the amount of enzyme that produces 1 μM of M-1-P per minute.

Example 2

Production of M-1-P-Producing Enzyme

The strain Corynebacterium glutamicum JCM1321 was employed. The bacterium was seeded in an SCD agar medium (Nihon Pharmaceutical Co., Ltd.) and allowed to grow overnight at 30° C. The grown bacterium was subjected to seed culture through the following steps; a medium (50 mL) containing 0.5% yeast extract, 4% amino acid seasoning solution K (Ajinomoto Co., Inc.), 3% maltose-rich syrup (Showa Sangyo Co., Ltd.), and 100 mM phosphate buffer (pH 7) was placed in a baffled Erlenmeyer flask; one platinum loop of the grown bacterium was seeded in the medium; and the bacterium was subjected to shaking culture overnight at 30° C., at 210 rpm. Primary culture of the thus-obtained seed bacterium was performed through the following steps; a medium (50 mL) containing 0.5% yeast extract, 1% amino acid seasoning solution K (Ajinomoto Co., Inc.), 0.5% ammonium sulfate, 10% dextrin MAX 1000 (Matsutani Chemical), 10% calcium chloride dihydrate, 200-ppm magnesium sulfate, 25-ppm ferric chloride, and 400 mM phosphate buffer (pH 7) was placed in a 160-baffled Erlenmeyer flask; the seed bacterium was seeded in the medium in an amount of 1%; and the bacterium was subjected to shaking culture overnight at 30° C., at 210 rpm.

In the supernatant of the medium, 240 U/L of the M-1-P-producing enzyme was produced.

Example 3

Isolation and Purification of M-1-P-Producing Enzyme

The primary culture broth (6 L) obtained in Example 2 was subjected to centrifugation, and the supernatant was concentrated through use of an ultrafiltration module ACP-13000 (Asahi Kasei Corporation), followed by dialysis with 10 mM phosphate buffer (pH 8). The concentrated dialysate was caused to run through a DEAE-Toyopearl 650M column (Tosoh Corporation; φ5×15 cm) for adsorption, and the column was washed with the same buffer (2 L), followed by elution with 1M sodium chloride (1.5 L), to thereby yield a crude enzyme solution.

The crude enzyme solution was purified by means of a BIO-CAD60 system (Perseptive). Specifically, 1M ammonium sulfate was firstly added to the crude enzyme solution (1,580 mL), and the mixture was caused to run, for adsorption, through a hydrophobic chromatography column POROS PE/M (φ10×100 mm) which had been equilibrated with 1M ammonium sulfate and 50 mM phosphate buffer. It was eluted with 150 ml of ammonium sulfate contained in 50 mM phosphate buffer (pH 8) with gradient of 1,000 mM to 360 mM, and then 375 mL of ammonia sulfate contained in 50 mM phosphate buffer (pH 8) with gradient of 360 mM to 0 mM at flow rate of 12 mL/minute. A fraction corresponding to about 360 mM ammonium sulfate was found to exhibit a peak attributed to the M-1-P-producing enzyme. The active fraction was dialyzed with 10 mM phosphate buffer (pH 8), thereby yielding 74 mL of an enzyme solution.

The dialyzed enzyme solution was further caused to run, for adsorption, through an anion exchange column POROS HQ/M (φ10×100 mm) which had been equilibrated with 20 mM phosphate buffer (pH 8). It was eluted with 450 mL of sodium chloride in 20 mM phosphate buffer (pH 8) with gradient of 0 to 50 mM was at flow rate of 12 mL/minute. Directly following the rise of sodium chloride concentration, an active fraction was obtained. The active fraction was dialyzed with 10 mM phosphate buffer (pH 8), thereby yielding 9.3 mL of an enzyme solution.

Further, the enzyme solution was applied to an anion exchange column POROS HQ/M (φ10×100 mm) in a manner similar to that described above. Directly following the rise of sodium chloride concentration, a peak which was believed to be attributed to the M-1-P-producing enzyme was detected.

The peak-top fraction was concentrated through use of a Centriprep YM-3 (Millipore) so as to attain a volume of 0.6 mL (i.e., the fraction was concentrated 10-fold). The concentrate was subjected to SDS-PAGE. A substantially single band was detected. The molecular weight was estimated to be 75 kDa. The amino acid sequence of an end of the amino moiety of the sample was determined to be Gly-Arg-Leu-Gly-Ile-Asp-Asp-Val-Arg-Pro-Arg-Ile-Leu-Asp-Gly-Asn-Pro-Ala-Lys-Ala-Val-Val-Gly-Glu-Ile-Val-Pro-Val-Ser-Ala-Ile-Val-Trp-Arg-Glu (the 3rd to 37th of SEQ ID NO: 2).

Example 4

Intracellular or Extracellular Activity of M-1-P-Producing Enzyme

The strains employed were *Corynebacterium glutamicum* JCM1318, *Corynebacterium hoagii* JCM1319, *Corynebacterium glutamicum* JCM1321, *Corynebacterium vitaeruminis* JCM1323, and *Corynebacterium callunae* IFO15359. Each of the bacteria was seeded in an SCD agar plate (Nihon Pharmaceutical Co., Ltd.) and cultured overnight at 30° C. Seed culture was performed through the following steps; 0.67% Yeast Nitrogen Base (Difco) (10 mL) was placed in a large test tube, and one platinum loop of the bacteria was seeded, followed by shaking-culture overnight at 30° C., at 250 rpm.

Primary culture was performed through shaking culture for 6 days at 35° C., at 250 rpm in a medium containing 0.67% Yeast Nitrogen Base (Difco) and 10% dextrin MAX 1000 (Matsutani Chemical) supplemented with or without 400 mM potassium phosphate buffer (pH 7.0).

The culture broth (1 mL) was subjected to centrifugation, to thereby separate the supernatant from cells. Extracellular activity of M1P-producing enzyme was determined through use of the supernatant without further treatment. Intracellular activity of M1P-producing enzyme was determined by use of the cells through the following steps; the thus-collected cells were suspended in 50 mM potassium phosphate buffer (pH 7.0) (an amount equal to that of the culture broth); the suspension was subjected to centrifugation thereby separating and washing the cells; the resultant cells were suspended in 50 mM potassium phosphate buffer (pH 7.0) (an amount equal to that of the culture broth); toluene (50 μL) was added to the suspension; the mixture was vigorously stirred for lysis of the cells to thereby yield an enzyme solution for measurement of activity; and the activity was measured in accordance with the method employed in Example 1. The results are shown in Table 1.

TABLE 1

|  |  | Without phosphate | | With 400 mM phosphate | |
| --- | --- | --- | --- | --- | --- |
|  |  | Intra-cellular | Extra-cellular | Intra-cellular | Extra-cellular |
| *Corynebacterium callunae* | IFO15359 | 20.37 | — | 631.33 | 326.58 |
| *Corynebacterium glutamicum* | JCM1321 | 10.02 | — | 177.88 | 485.21 |
| *Corynebacterium vitaeruminis* | JCM1323 | 5.55 | — | 281.25 | 40.60 |
| *Corynebacterium hoagii* | JCM1319 | 4.46 | — | 293.57 | 211.84 |
| *Corynebacterium glutamicum* | JCM1318 | 4.33 | — | 228.26 | 208.81 |

The results indicate the following. When no phosphate is added, the enzyme exhibits activity only inside cells. When the bacterium is cultured in the presence of high concentration of phosphate, the M-1-P-producing enzyme activity is improved, and M-1-P-producing enzyme produced inside cell are released to the culture broth.

Example 5

Optimum pH and Active pH

As substrates, 2% maltoheptaose (G7: Seikagaku Corporation) and 700 mM phosphate buffers of each pH from 5.5 to 8.5 were employed. The purified enzyme was added to the substrates so as to attain a concentration of 0.28 U/mL, and the mixture was allowed to react for 1 hour at 37° C. The reaction mixture was treated for 10 minutes at 95° C. to stop the reaction, and the mixture was diluted 101-fold, followed by quantification of M-1-P through HPLC in a manner similar to that employed in Example 1.

Figure 1:
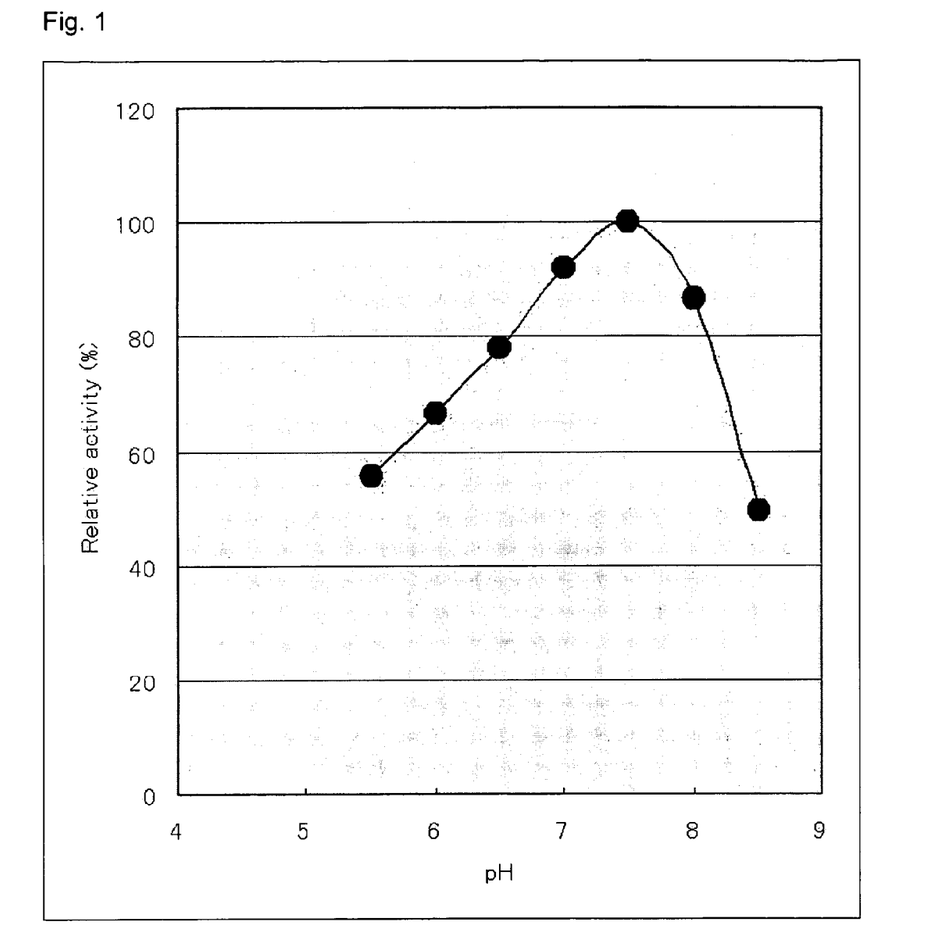
FIG. 1 shows a pH vs. activity curve of the enzyme of the present invention.

The results are shown in FIG. 1. The optimum pH was found to be about 6.5 to about 8.0. In this range, the enzyme exhibits 80% or more of the activity measured at pH 7.5 (the maximum activity). At a pH ranging from 5.5 to 8.5, the enzyme exhibits 50% or more of the activity measured at pH 7.5, revealing that the enzyme is active in a wide pH range.

Example 6

Optimum Temperature and Active Temperature

Figure 2:
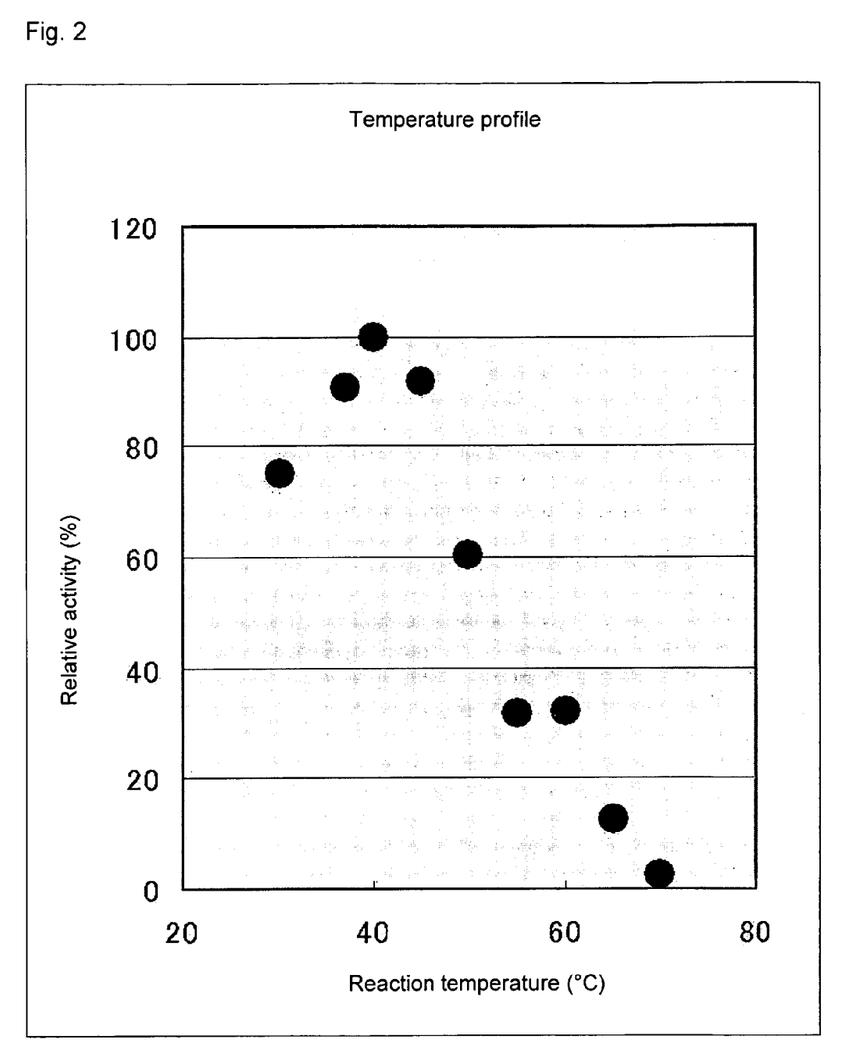
FIG. 2 shows a temperature vs. activity curve of the enzyme of the present invention.

As substrates, 1M potassium phosphate buffer (pH 7) and 2% maltoheptaose (G7: Seikagaku Corporation) were employed. The purified enzyme was added to the substrates so as to attain a concentration of 0.168 U/mL, and the mixture was allowed to react for 1 hour at a temperature of 30° C. to 70° C. The reaction mixture was treated for 10 minutes at 95° C. for deactivation of the enzyme. The reaction mixture was diluted 101-fold, followed by quantification of M-1-P through HPLC in a manner similar to that described in Example 1. The results are shown in FIG. 2. The optimum temperature was found to be 35° C. to 50° C. In the range, the enzyme exhibits 60% or more of the activity measured at 40° C. (the maximum activity). In a wide temperature range (30° C. to 55° C.), the enzyme exhibits 30% or more of the activity measured at 40° C.

Example 7

Substrate Specificity (1) Production of M-1-P from Dextrin and Phosphate

To 2.5% Dextrin MAX 1000 (Matsutani Chemical) and 250 mM phosphate buffer (pH 7), 0.16 U/mL M-1-P-producing enzyme was added, and the mixture was allowed to react for 15 hours at 37° C. In a manner similar to that described in Example 1, M-1-P was quantified. The enzyme was found to produce 145 µM M-1-P.

(2) Production of M-1-P from Phosphate and Different Maltooligosaccharides

To 250 mM Phosphate buffer (pH 7) and each of substrates having different chain lengths (glucose, maltose, maltotriose, maltotetraose, maltopentaose, maltohexaose (Seikagaku Corporation)) (2.5%), 0.16 U/mL M-1-P-producing enzyme was added, and the mixture was allowed to react for 15 hours at 37° C. In a manner similar to that described in Example 1, M-1-P was quantified. The results are shown in Table 2.

TABLE 2

| Substrate | Amount of maltose-1-phosphate produced (µM) |
|---|---|
| Glucose | ND |
| Maltose | ND |
| Maltotriose | ND |
| Maltotetraose | ND |
| Maltopentaose | 1.04 |
| Maltohexaose | 49.6 |
| Maltoheptaose | 96.1 |

(3) Maltose Transfer Reaction 0.16 U/mL M-1-P-producing enzyme was allowed to react with each of the substrates having different chain lengths (glucose, maltose, maltotriose, maltotetraose, maltopentaose, maltohexaose (Seikagaku Corporation)) (2.0%) for one hour at 37° C., and the reaction mixture was subjected to HPLC for analysis in a manner similar to that described in Example 1 (the results are represented as peak area). The retention times of maltooligosaccharides (DP=1 to 11) were estimated through analysis of dextrin (Matsutani Chemical). The results are shown in Table 3.

TABLE 3

| Product Peak area × $10^6$ | Substrate | | | | | | |
|---|---|---|---|---|---|---|---|
| | Glucose | Maltose | DP = 3 | DP = 4 | DP = 5 | DP = 6 | DP = 7 |
| Glucose | 65.97 | 0.19 | 0.52 | 0.19 | 0.09 | 0.05 | 0.11 |
| Maltose | 0.00 | 46.79 | 1.84 | 0.15 | 0.27 | 0.61 | 0.28 |
| DP = 3 | 0.00 | 0.27 | 33.27 | 1.25 | 0.51 | 0.37 | 0.12 |
| DP = 4 | 0.00 | 0.00 | 0.12 | 30.80 | 0.58 | 10.20 | 0.19 |
| DP = 5 | 0.00 | 0.00 | 0.00 | 0.00 | 26.40 | 0.00 | 9.59 |
| DP = 6 | 0.00 | 0.00 | 0.00 | 0.36 | 0.00 | 8.87 | 0.00 |
| DP = 7 | 0.00 | 0.00 | 0.00 | 0.00 | 0.52 | 0.00 | 6.36 |
| DP = 8 | 0.00 | 0.00 | 0.00 | 0.00 | 0.00 | 5.04 | 0.00 |
| DP = 9 | 0.00 | 0.00 | 0.00 | 0.00 | 0.00 | 0.00 | 3.42 |
| DP = 10 | 0.00 | 0.00 | 0.00 | 0.00 | 0.00 | 3.96 | 0.00 |
| DP = 11 | 0.00 | 0.00 | 0.00 | 0.00 | 0.00 | 0.00 | 3.47 |

Example 8

Cloning of M-1-P-Producing Enzyme Gene

*Corynebacterium glutamicum* JCM1321 cells were cultured overnight in a Trypticase Soy Broth medium (BBL) at 30° C. The culture broth (10 mL) was subjected to centrifugation to collect the cells, and the cells were processed through the process described in Manual of Industrial Microbiology and Biotechnolory, 379-391 (1999), ASM press, Washington D.C., to thereby prepare chromosomal DNA molecules.

Primer 1 (5'-GAYGGNAAYCCNGCNAARGCNGT (SEQ ID NO: 3)) and primer 2 (5'-GCNGTNGTNGGN-GARATHGTNCC (SEQ ID NO: 4)) were designed from Asp-Gly-Asn-Pro-Ala-Lys-Ala-Val (the 16th to 23rd of SEQ ID NO: 2) and Ala-Val-Val-Gly-Glu-Ile-Val-Pro (the 22nd to 29th of SEQ ID NO: 2), respectively, contained in the N-terminal amino acid sequence obtained in Example 3. An LA PCR in vitro cloning kit (product of Takara Bio Inc.) was employed for gene amplification. Specifically, the chromosomal DNA molecules prepared above were cleaved through use of a restriction enzyme HindIII, and the product was ligated to a HindIII cassette attached to the kit. PCR was performed through use of the primer 1 and the cassette primer C1 (30 cycles, 94° C., 30 sec→60° C., 30 sec→72° C., 4 min). The reaction mixture was diluted 100-fold, to thereby prepare a template. PCR was performed through use of the template and through use of the primer 2 and a cassette primer C2 (30 cycles, 94° C., 30 sec→60° C., 30 sec→72° C., 4 min). The amplified fragments were found to have a length of about 2 kb. The fragments were found to have a nucleotide sequence encoding the N-terminal amino acid sequence obtained in Example 3. Further, in order to obtain an upstream region of the 2-kb fragment, the chromosomal DNA molecules were cleaved through use of EcoRI, and the product was ligated to an EcoRI cassette. The first PCR was performed through use of primer 3 (5'-TGAATAGGCT-CAGCCGCCACTGAAGAATCC (SEQ ID NO: 5)) and cassette primer C1 for the upstream region, and for downstream region, primer 4 (5'-TCAGATCATCGCCTACTC-CAAGGTTGAT (SEQ ID NO: 6)) and cassette primer C1 were used. The thus-obtained reaction mixture was diluted 100-fold, to thereby prepare a template. The second PCR was performed through use of primer 5 (5'-ACGCCACA-CAATAGCCGAGACAGG (SEQ ID NO: 7)) for the upstream region and through use of primer 6 (5'-CTGTG-GTCAGAGACGAACTTTGTCCGCCTC (SEQ ID NO: 8)) and cassette primer C2 for down stream region (30 cycles, 94° C., 30 sec→60° C., 30 sec→72° C., 4 min). The thus-amplified upstream and downstream fragments were found to have a length of about 0.4 kb and about 1 kb, respectively. The sequences of the thus-obtained fragments were determined. Through use of primer 7 (5'-GGAGAGAT-TCGTCATTGAGTTCACTCG (SEQ ID NO: 9)) designed from the sense chain in the upstream region and primer 8 (5'-TCAGCCCGCTCGCGGTGACCTAAGTC (SEQ ID NO: 10)) designed from the antisense chain, fragments having a length of about 2.6 kb were amplified by use of the chromosomal DNA as a template by means of Pyrobest polymerase (Takara Bio Inc.) (25 cycles, 94° C., 30 sec→55° C., 30 sec→72° C., 3 min). The entire nucleotide sequence of the fragments are shown in SEQ ID NO: 1. The sequence was found to have a 2025-bp open reading frame region encoding deducted 675 amino acid residues.

The 675 amino acid residues deducted from the nucleotide sequence was subjected to BLASTP homology search in the NCBI database, revealing that the sequence exhibits 99% to 38% homology with proteins originating from *Corynebacterium glutamicum* ATCC13032; 99%, *Corynebacterium efficiens* YS-314; 84%, *Corynebacterium diphtheriae*; 66%, *Mycobacterium smegmatis*; 60%, *Mycobacterium tuberculosis* CDC1551; 58%, *Mycobacterium bovis* subsp. *Bovis* AF2122/97; 58%, *Mycobacterium avium* subsp. *Paratuber culosisstr.* K10; 58%, *Streptomyces avermitilis* MA-4680; 53%, *Thermobifida fusca*; 53%, *Streptomyces coelicolor* A3 (2); 52%, *Pseudomonas aeruginosa* PA01; 43%, *Pseudomonas aeruginosa* UCBPP-PA14; 43%, *Pseudomonas syringae* pv. *tomato str.* DC3000; 42%, *Chloroflexus aurantiacus*; 42%, *Chlorobium tepidum* TLS; 41%, *Bifidobacterium Longum* NCC2705; 39%, *Rhodospirillum rubrum*; 42%, *Ralstonia solanacearum*; 41%, *Bifidobacter iumLongum* DJ010A; 39%, *Pseudomonas putida* KT2440; 44%, *Rhodopseudomonas palustris*; 41%, *Azotobacter vinelandii*; 43%, *Burkholderia fungorum*; 42%, *Rhodobacter sphaeroides*; 41%, *Pseudomonas fluorescens* Pf0-1; 42%, *Xanthomonas campestris str.* ATCC33913; 42%, *Xanthomonas axonopodis pv. ctri str.* 306; 41%, *Bordetella bronchiseptica* RB50; 40%, and *Bradyrhizobium japonicum* USDA110; 38%. These proteins are classified into the Family 13 of Glycosyl Hydrolase in the saccharide-related enzyme database CAZy, and deduced to be glycosidase, amylase, glucanase, or the like. However, the deduction is merely based on the genomic sequence of these proteins. Genes of the proteins have never been isolated, and genes to produce the proteins has never been expressed. Thus, nothing has been known in relation to the function. Comparison with the amino acid sequences in terms of alignment reveals highly conserved regions of the 342nd to 352nd amino acid residues (Ala-Glu-Asn-Pro-Pro-Lys-Lys(or Arg)-Tyr-Gln(or Glu)-Asp-Ile) [see the 342nd to 352nd of SEQ ID NO: 2; SEQ ID NO: 11] and the 383rd to 392nd amino acid residues (Phe-Arg-Val(or Ile)-Asp-Asn-Pro-His-Thr-Lys-Pro) [see the 383rd to 392nd of SEQ ID NO: 2; SEQ ID NO: 12] from the N-terminus of the amino acid sequence of the M-1-P-producing enzyme of the present invention.

Example 9

Expression in *E. coli*

The 2.6-kb fragment obtained in Example 8 was inserted into an *E. coli* expression vector pUC19 at the SmaI site thereof. Specifically, the PCR fragment (2.5 μg) is treated with T4-polynucleotide kinase (Takara Bio Inc.) to thereby phosphorylate the end, and pUC19 (1 μg) was cleaved through use of SmaI and then treated with alkaline phosphatase (Roche). The both fragments were treated for 30 minutes at 65° C. for deactivation of the enzyme, then mixed together, and subjected to ethanol precipitation. After drying under reduced pressure, the fragments were ligated together through use of a ligation kit Ver2 (Takara Bio Inc.). Transformation was performed through use of an *Escherichia coli* JM109 Competent Cells (Takara Bio Inc.), and proliferation was performed in an LB agar medium (1% yeast extract (Difco), 0.5% trypton (Difco), 1% sodium chloride, 1% agar, 25 μg/mL ampicillin). The formed colonies were subjected to shaking culture overnight at 37° C. in an LB medium (1% yeast extract (Difco), 0.5% trypton (Difco), 1% sodium chloride, 25 μg/mL ampicillin). The cells were collected. Preparation of plasmid was performed through use of a plasmid isolation kit (Roche). A plasmid (pUMP2) into which the fragment is inserted in the same direction as that of the LacZ promoter of pUC19 and a plasmid (pUMP3) into which the fragment is inserted in the direction opposite to that of the LacZ promoter were obtained.

Each of transformants of the plasmides was cultured overnight at 37° C. in an LB medium (2 mL) containing 25 μg/mL ampicillin, the medium being supplemented with or without 1 mM IPTG (isopropyl 1-thio-β-D-galactoside). The cultured cells were collected, suspended in 0.5 mL of 50 mM phosphate buffer (pH 7), and pulverized by means of an ultrasound pulverizer. The resultant solution was measured in terms of M-1-P producing activity in a manner similar to that described in Example 1. The results are shown in Table 4.

TABLE 4

| Plasmid | Medium | Maltose-1-phosphate producing acitivity (U/L) in culture broth |
|---------|--------|---------------------------------------------------------------|
| pUMP2   | IPTG−  | 24.1 |
| pUMP2   | IPTG+  | 41.5 |
| pUMP3   | IPTG−  | 11.7 |
| pUMP3   | IPTG+  | 13.6 |

Example 10

Method for Producing M-1-P

The cell strains employed were *Corynebacterium* sp. JCM1300, *Corynebacterium flavescens* JCM1317, *Corynebacterium glutamicum* JCM1318, *Corynebacterium hoagii* JCM1319, *Corynebacterium glutamicum* JCM1321, *Corynebacterium vitaeruminis* JCM1323, *Corynebacterium pilosum* JCM3714, *Corynebacterium amycolatum* JCM7447, *Corynebacterium matruchotii* JCM9386, *Corynebacterium minutissimum* JCM9387, *Corynebacterium striatum* JCM9390, and *Corynebacterium callunae* IFO15359. Each of the cells was seeded in an SCD agar plate (Nihon Pharmaceutical Co., Ltd.) and incubated overnight at 30° C. Seed culture was performed through the following steps; 10 mL of 0.67% Yeast Nitrogen Base (Difco) was added to a large test tube, one platinum loop of the cell was seeded in the test tube, and shaking culture was performed overnight at 30° C., at 250 rpm.

Primary culture was performed through shaking culture for 6 days at 35° C., at 250 rpm in a medium containing 0.67% Yeast Nitrogen Base (Difco), 10% dextrin MAX 1000 (Matsutani Chemical), and 400 mM potassium phosphate buffer (pH 7.0).

M-1-P contained in the supernatant was quantified by means of a DX500 chromatography system (DIONEX).

Quantification was performed through use of the following; column: CarboPac PA1 (Nippon Dionex K.K. 4×250 mm), detector: ED40 pulsed amperometric detector, eluent: solution A; 100 mM sodium hydroxide, solution B; 100 mM sodium hydroxide containing 1M sodium acetate.

Linear gradient analysis was employed (initial concentration: solution A 90%: solution B 10%, 0-17 min.: solution A 18.5%: solution B 81.5%). As standard substances, 100 mM and 50 mM M-1-P products (product of SIGMA) were employed. A peak was observed at about 15.5 minutes. The supernatant of the culture broth was diluted 200-fold, and 20 μL of the dilution was injected. The analysis results are shown in Table 5.

TABLE 5

| Strain | Amount of M-1-P produced (g/L) |
|---|---|
| Corynebacterium sp. JCM1300 | 1.5 |
| Corynebacterium flavescens JCM1317 | 0.2 |
| Corynebacterium glutamicum JCM1318 | 0.7 |
| Corynebacterium hoagii JCM1319 | 1.8 |
| Corynebacterium glutamicum JCM1321 | 3.1 |
| Corynebacterium vitaeruminis JCM1323 | 0.3 |
| Corynebacterium pilosum JCM3714 | 0.2 |
| Corynebacterium amycolatum JCM7447 | 0.1 |
| Corynebacterium matruchotii JCM9386 | 0.1 |
| Corynebacterium minutissimum JCM9387 | 0.2 |
| Corynebacterium striatum JCM9390 | 0.3 |
| Corynebacterium callunae IFO15359 | 4.0 |

The results indicate that M-1-P can be produced by culturing a bacterium belonging to the family Corynebacterium in a medium containing phosphate and an oligosaccharide or polysaccharide having an α-1,4-glycosidic bond. The supernatant of the culture broth may also contain, in addition to M-1-P, glucose-1-phosphate or a similar phosphorylated saccharide produced. Therefore, M-1-P was isolated by separating and removing the cells, subjecting the supernatant to ultrafiltration, reverse osmosis membrane, electrodialysis, ion exchanged membrane, ion exchanged resin, active carbon, synthetic absorbent, crystallization, or a similar treatment in accordance with needs, and then subjecting to ion exchange chromatography.

Referential Example 1

Production of Phophorylase through Use of a Bacterium Belonging to the Family Corynebacterium Each of Corynebacterium vitaeruminis JCM1323 and Corynebacterium callunae IFO15359 cells was seeded in an SCD agar medium (Nihon Pharmaceutical Co., Ltd.) and cultured at 30° C. One platinum loop of the thus-obtained bacterium was seeded in a liquid medium (0.67% Yeast Nitrogen Base (Difco 社), each of 50, 100, and 200 mM phosphate buffers (pH 7), 15% dextrin (sigma, originating from potato)), and subjected to shaking culture for 6 days at 30° C. The cells contained in the culture broth were removed through centrifugation, and the maltodextrin phosphorylase activity of the supernatant was measured.

The maltodextrin phosphorylase activity of the supernatant was measured through a partially-modified method of Weinhausel (Enzyme Microb. Technol., 17, 140-146 (1995)). Specifically, to a 96-well microplate, were added each of the culture broth supernatant samples (20 μL) which had been appropriately diluted and an enzyme reaction solution (180 μL) (200 mM potassium phosphate buffer (pH 7.0), 2% dextrin, 100 mM Tris-acetate buffer (pH 6.8), 2 mM EDTA, 10 mM magnesium sulfate, 2 mM NAD, 10 mM glucose-1,6-diphosphate, 1.2 unit/mL phosphoglucomutase (originating from rabbit muscle, product of Roche Diagnostics K.K.), 1.2 unit/mL glucose-6-phosphate dehydrogenase (originating from Leuconostoc mesenteroides, product of Roche Diagnostics K.K.)). Increase in absorbance at 340 nm attributed to G1P production was measured at 37° C. One enzyme unit (U) is defined as the amount of enzyme that produces 1 μmol of glucose-1-phosphate (G1P) per minute. The results are shown in Table 6.

TABLE 6

| | Extracellular maltodextrin phosphorylase (U/L) | | |
|---|---|---|---|
| | Phosphate concentration | | |
| | 50 | 100 | 200 |
| C. vitaeruminis | 7.1 | 134.0 | 90.3 |
| C. callunae | 0 | 3.6 | 42.0 |

As shown in Table 6, by increasing phosphate concentration in medium, maltodextrin phosphorylase was extracellularly released. Thus, when the region of the gene encoding the enzyme was removed from the genome, or the enzyme is deactivated, only M-1-P can be produced without production of glucose-1-phosphate.

The present application is a continuation of PCT/JP2005/009501, filed on May 18, 2005, the entire contents of which are incorporated herein by reference.

The invention claimed is:

1. An isolated maltose-1-phosphate-producing enzyme which has an amino acid sequence that is at least 90% homologous to SEQ ID NO: 2 and the following enzymatic characteristics;
   1) Action: producing maltose-1-phosphate from a phosphoric acid or a salt thereof and an oligosaccharide or polysaccharide containing an α-1,4-glycosidic bond and having a glucose polymerization degree of 5 or more,
   2) Substrate specificity: in the presence of a phosphoric acid or a salt thereof, effectively acting on oligosaccharide or polysaccharide containing an α-1,4-glucosidic bond and having a glucose polymerization degree of 6 or more thereby producing maltose-1-phosphate; weakly acting on an oligosaccharide having a glucose polymerization degree of 5; and exhibiting substantially no action on an oligosaccharide having a polymerization degree of 2 to 4,
   3) Molecular weight: about 75 kDa (SDS-PAGE),
   4) Optimum pH: 6.5 to 8.0, and
   5) Optimum temperature: 35 to 50° C.

2. An isolated maltose-1-phosphate-producing enzyme having the amino acid sequence of SEQ ID NO: 2.

3. An isolated maltose-1-phosphate-producing enzyme having an amino acid sequence represented by SEQ ID NO: 2 in which one to ten amino acid residues are deleted, substituted, or added, and which produces maltose-1-phosphate.

4. An isolated maltose-1-phosphate-producing enzyme of claim 1 which has an amino acid sequence that is at least 90% homologous to SEQ ID NO: 2, produces a maltose-1-phosphate, and contains an amino acid sequence represented by Ala-Glu-Asn-Pro-Pro-Lys-Lys(or Arg)-Tyr-Gln(or Glu)-Asp-Ile (SEQ ID NO: 11) and/or Phe-Arg-Val(or Ile)-Asp-Asn-Pro-His-Thr-Lys-Pro (SEQ ID NO: 12).

5. The maltose-1-phosphate-producing enzyme of claim 4, wherein said amino acid sequence contains an amino acid sequence represented by Ala-Glu-Asn-Pro-Pro-Lys-Lys(or Arg)-Tyr-Gln(or Glu)-Asp-Ile (SEQ ID NO: 11).

6. The maltose-1-phosphate-producing enzyme of claim 4, wherein said amino acid sequence contains an amino acid sequence represented by Phe-Arg-Val(or Ile)-Asp-Asn-Pro-His-Thr-Lys-Pro (SEQ ID NO: 12).

7. The maltose-1-phosphate-producing enzyme of claim 4, wherein said amino acid sequence contains an amino acid sequence represented by Ala-Glu-Asn-Pro-Pro-Lys-Lys(or Arg)-Tyr-Gln(or Glu)-Asp-Ile (SEQ ID NO: 11) and an amino acid sequence represented by Phe-Arg-Val(or Ile)-Asp-Asn-Pro-His-Thr-Lys-Pro (SEQ ID NO: 12).

8. An isolated maltose-1-phosphate-producing enzyme which has an amino acid sequence that is at least 95% homologous to SEQ ID NO: 2, produces a maltose-1-phosphate, and contains an amino acid sequence represented by Ala-Glu-Asn-Pro-Pro-Lys-Lys(or Arg)-Tyr-Gln(or Glu)-Asp-Ile (SEQ ID NO: 11) and/or Phe-Arg-Val(or Ile)-Asp-Asn-Pro-His-Thr-Lys-Pro (SEQ ID NO: 12).

* * * * *

SEQUENCE LISTING

<160> NUMBER OF SEQ ID NOS: 12

<210> SEQ ID NO 1
<211> LENGTH: 2556
<212> TYPE: DNA
<213> ORGANISM: Corynebacterium glutamicum JCM1321
<220> FEATURE:
<221> NAME/KEY: CDS
<222> LOCATION: (247)..(2271)

<400> SEQUENCE: 1
ggagagaatt cgtcattgag ttcactcgaa tcagagggaa aagatgcagc tgcagagtta      60
tttaaagagt tagtcacatc tcccatcttg actgatttct ccggttccgt gtggaagtga     120

-continued

```
cacagctccg ttaagctttc ataatggaga catacccccg gctaattgcc ggtgtgtctg      180
cttgatcgaa ctttttaagct tgtgtgcgtt tgttcgcact tcacactgca tgttgaggag    240
```

| | | | | | | | | | | | | | | |
|---|---|---|---|---|---|---|---|---|---|---|---|---|---|---|

```
aaaact gtg act ggc cgt ctc ggt atc gat gat gtt cgt ccc cgg att        288
       Val Thr Gly Arg Leu Gly Ile Asp Asp Val Arg Pro Arg Ile
        1               5                  10 ttg gat gga aat cca gcg aaa gca gta gtg ggt gag att gtt cct gtc       336
Leu Asp Gly Asn Pro Ala Lys Ala Val Val Gly Glu Ile Val Pro Val
15              20                  25                  30 tcg gct att gtg tgg cgt gaa ggc cat gat gca att gcc gcg acg ttg       384
Ser Ala Ile Val Trp Arg Glu Gly His Asp Ala Ile Ala Ala Thr Leu
                 35                  40                  45 aat gtt tcc ggt ccg gag gat tct tca gtg gcg gct gag cct att cag       432
Asn Val Ser Gly Pro Glu Asp Ser Ser Val Ala Ala Glu Pro Ile Gln
        50                  55                  60 att cat atg cgc ccc act cct gat aat cag gat cag tcg aat gca ttt       480
Ile His Met Arg Pro Thr Pro Asp Asn Gln Asp Gln Ser Asn Ala Phe
            65                  70                  75 ttc gtt cct gat gtc cct ggt aat tgg aca ttt cgt gtg gat gcg tgg       528
Phe Val Pro Asp Val Pro Gly Asn Trp Thr Phe Arg Val Asp Ala Trp
        80                  85                  90 tcg gat cct atg gct aca tgg cgt cat gcg att acc act aaa att gag       576
Ser Asp Pro Met Ala Thr Trp Arg His Ala Ile Thr Thr Lys Ile Glu
95                  100                 105                 110 gca ggc cag ggt tca gat gag ttg tat aac gac ttc gag cac ggg gct       624
Ala Gly Gln Gly Ser Asp Glu Leu Tyr Asn Asp Phe Glu His Gly Ala
                115                 120                 125 cag ctg ttt gaa cgg gct gcg gag aat ttg tct aaa gag gat agg act       672
Gln Leu Phe Glu Arg Ala Ala Glu Asn Leu Ser Lys Glu Asp Arg Thr
            130                 135                 140 gcg ctt ttc gac gtc gcc tcc tct ctg cgg cgc ggc ggc gat gta cgc       720
Ala Leu Phe Asp Val Ala Ser Ser Leu Arg Arg Gly Gly Asp Val Arg
        145                 150                 155 gca cgt ctc gcc cca gcg ctc acc tcg agt gtc act cat ctt tta gaa       768
Ala Arg Leu Ala Pro Ala Leu Thr Ser Ser Val Thr His Leu Leu Glu
    160                 165                 170 ctt aac ccg ttg cgt gag ttg gtc acg atg ggt gaa aac ctg cag gtt       816
Leu Asn Pro Leu Arg Glu Leu Val Thr Met Gly Glu Asn Leu Gln Val
175                 180                 185                 190 cgt gtc gag cgt cgt gcc gct ttg gtc aac tct tgg tat gag ctt ttc       864
Arg Val Glu Arg Arg Ala Ala Leu Val Asn Ser Trp Tyr Glu Leu Phe
                195                 200                 205 cct cgt tcc aca ggt ggt tgg gat gag tcc ggc acc ccc gtt cat ggc       912
Pro Arg Ser Thr Gly Gly Trp Asp Glu Ser Gly Thr Pro Val His Gly
            210                 215                 220 act ttc gct acc act gct cag gcg ttg gag cgt gtc gcg aag atg ggc       960
Thr Phe Ala Thr Thr Ala Gln Ala Leu Glu Arg Val Ala Lys Met Gly
        225                 230                 235 ttc gat act gtt tac ttc ccg ccg atc cat ccg att ggc gag gtc aac      1008
Phe Asp Thr Val Tyr Phe Pro Pro Ile His Pro Ile Gly Glu Val Asn
    240                 245                 250 cgc aag ggc cgc aat aat acg ctg acc ccg gaa cct cat gat gtg ggt      1056
Arg Lys Gly Arg Asn Asn Thr Leu Thr Pro Glu Pro His Asp Val Gly
255                 260                 265                 270 tcg ccg tgg gct att ggt tct aaa gat ggt ggg cat gat gca acg cat      1104
Ser Pro Trp Ala Ile Gly Ser Lys Asp Gly Gly His Asp Ala Thr His
                275                 280                 285 ccg cgg ttg ggc acc att gaa gat ttc cag gcg ttg ttg gct cgc gca      1152
Pro Arg Leu Gly Thr Ile Glu Asp Phe Gln Ala Leu Leu Ala Arg Ala
            290                 295                 300
```

```
cgg gaa ctc aat ttg gaa gtt gca ctc gat cta gct ctg cag gct gcc    1200
Arg Glu Leu Asn Leu Glu Val Ala Leu Asp Leu Ala Leu Gln Ala Ala
        305                 310                 315 cct gat cat cca tgg gcg cag gaa cac cgc gag ttt ttc acg gtg ttg    1248
Pro Asp His Pro Trp Ala Gln Glu His Arg Glu Phe Phe Thr Val Leu
320                 325                 330 gct gat ggc acc att gcg tat gca gaa aac cca ccg aag aag tac cag    1296
Ala Asp Gly Thr Ile Ala Tyr Ala Glu Asn Pro Pro Lys Lys Tyr Gln
335                 340                 345                 350 gat att tat ccc atc aac ttt gat aat gct gct ccg agg atc tat gaa    1344
Asp Ile Tyr Pro Ile Asn Phe Asp Asn Ala Ala Pro Arg Ile Tyr Glu
            355                 360                 365 gag gtc tat cgt gtg gtg aag ttc tgg gtg gat ttg ggt gtg acc aca    1392
Glu Val Tyr Arg Val Val Lys Phe Trp Val Asp Leu Gly Val Thr Thr
            370                 375                 380 ttc cgc gtg gat aac ccg cac act aag ccc gct aat ttc tgg cag tgg    1440
Phe Arg Val Asp Asn Pro His Thr Lys Pro Ala Asn Phe Trp Gln Trp
                385                 390                 395 ctt att tct gcc atc cat aaa tca aac cct gag gtc att ttc cta gcg    1488
Leu Ile Ser Ala Ile His Lys Ser Asn Pro Glu Val Ile Phe Leu Ala
400                 405                 410 gag gcg ttt act cgc ccg gca cgt ctg tat ggc ttg gcc aag att ggt    1536
Glu Ala Phe Thr Arg Pro Ala Arg Leu Tyr Gly Leu Ala Lys Ile Gly
415                 420                 425                 430 ttc tcc cag tct tac acc tac ttc acg tgg aag gtc acc aag gag gag    1584
Phe Ser Gln Ser Tyr Thr Tyr Phe Thr Trp Lys Val Thr Lys Glu Glu
                435                 440                 445 ctc acc gag ttc gct act gag atc gcc cgc atg gcg gat att tct cgt    1632
Leu Thr Glu Phe Ala Thr Glu Ile Ala Arg Met Ala Asp Ile Ser Arg
            450                 455                 460 ccg aac ctg ttt gtg aac act ccc gac att ttg cat gcg tct ctg cag    1680
Pro Asn Leu Phe Val Asn Thr Pro Asp Ile Leu His Ala Ser Leu Gln
            465                 470                 475 cat ggt gga cgc gca atg ttc gct atc cgc gcc gca ttg gcc gcc acg    1728
His Gly Gly Arg Ala Met Phe Ala Ile Arg Ala Ala Leu Ala Ala Thr
        480                 485                 490 atg tct cct gtg tgg ggc gtg tac tcc gga tat gag ctt ttt gag cat    1776
Met Ser Pro Val Trp Gly Val Tyr Ser Gly Tyr Glu Leu Phe Glu His
495                 500                 505                 510 gag gca gtg aag cct ggc tcg gag gag tac ttg gat tct gag aag tac    1824
Glu Ala Val Lys Pro Gly Ser Glu Glu Tyr Leu Asp Ser Glu Lys Tyr
                515                 520                 525 gaa ctg cgt ccc cgc gat ttc aag ggt gct ctg gaa cgt ggc gat tct    1872
Glu Leu Arg Pro Arg Asp Phe Lys Gly Ala Leu Glu Arg Gly Asp Ser
            530                 535                 540 ctc gag gat tac atc gct ctg ctc aac cag atc cgt gcg aac cct        1920
Leu Glu Asp Tyr Ile Ala Leu Leu Asn Gln Ile Arg Arg Ala Asn Pro
        545                 550                 555 gcc ttg cag cag cta cgc aac atc cac ttc cac gaa gcg gac aat gat    1968
Ala Leu Gln Gln Leu Arg Asn Ile His Phe His Glu Ala Asp Asn Asp
        560                 565                 570 cag atc atc gcc tac tcc aag gtt gat gct ttg acc gga aat acc gtg    2016
Gln Ile Ile Ala Tyr Ser Lys Val Asp Ala Leu Thr Gly Asn Thr Val
575                 580                 585                 590 ttg att gtg gtc aac ttg gat cca cgt agt gct cgt gag gct act gtt    2064
Leu Ile Val Val Asn Leu Asp Pro Arg Ser Ala Arg Glu Ala Thr Val
                595                 600                 605 cgc ctt gat ctt gga gcg ctt ggc tta gaa gcg ggt gca cag ttt gag    2112
Arg Leu Asp Leu Gly Ala Leu Gly Leu Glu Ala Gly Ala Gln Phe Glu
```

-continued

```
                610                 615                 620
gtg cgc gat gcg atc acc gac tcc cgt tac ctg tgg tca gag acg aac      2160
Val Arg Asp Ala Ile Thr Asp Ser Arg Tyr Leu Trp Ser Glu Thr Asn
            625                 630                 635 ttt gtc cgc ctc gag ccc cta cgc gat gtc gcc cac atc ttt gtt ctt      2208
Phe Val Arg Leu Glu Pro Leu Arg Asp Val Ala His Ile Phe Val Leu
        640                 645                 650 cct gaa ctt cca gcg tct cgc cgt gaa cgt ctt gca tgg cgc gaa atc      2256
Pro Glu Leu Pro Ala Ser Arg Arg Glu Arg Leu Ala Trp Arg Glu Ile
655                 660                 665                 670 aaa acc tac cgc gcg taatttccca tctctgtacc ttctatcaag gattatcatc      2311
Lys Thr Tyr Arg Ala
                675 atgaccgttg accccgcgag ccacatcacc atccctgagg cagatctggc ccgcctgcgc    2371 cactgcaacc atcacgatcc tcacgggttt tatggttggc atgagaccga agctggttcg    2431 gttatccgca cgcgccagat cggcgcaacg caggttaatt tgcttatcga cgacacctcc    2491 cacgtcatga ccccaatcgg cgacgacatt ttcgcaattg acttaggtca ccgcgagcgg    2551 gctga                                                                2556

<210> SEQ ID NO 2
<211> LENGTH: 675
<212> TYPE: PRT
<213> ORGANISM: Corynebacterium glutamicum JCM1321

<400> SEQUENCE: 2

Val Thr Gly Arg Leu Gly Ile Asp Asp Val Arg Pro Arg Ile Leu Asp
1               5                   10                  15

Gly Asn Pro Ala Lys Ala Val Val Gly Glu Ile Val Pro Val Ser Ala
            20                  25                  30

Ile Val Trp Arg Glu Gly His Asp Ala Ile Ala Ala Thr Leu Asn Val
        35                  40                  45

Ser Gly Pro Glu Asp Ser Ser Val Ala Ala Glu Pro Ile Gln Ile His
    50                  55                  60

Met Arg Pro Thr Pro Asp Asn Gln Asp Gln Ser Asn Ala Phe Phe Val
65                  70                  75                  80

Pro Asp Val Pro Gly Asn Trp Thr Phe Arg Val Asp Ala Trp Ser Asp
                85                  90                  95

Pro Met Ala Thr Trp Arg His Ala Ile Thr Thr Lys Ile Glu Ala Gly
            100                 105                 110

Gln Gly Ser Asp Glu Leu Tyr Asn Asp Phe Glu His Gly Ala Gln Leu
        115                 120                 125

Phe Glu Arg Ala Ala Glu Asn Leu Ser Lys Glu Asp Arg Thr Ala Leu
    130                 135                 140

Phe Asp Val Ala Ser Ser Leu Arg Arg Gly Gly Asp Val Arg Ala Arg
145                 150                 155                 160

Leu Ala Pro Ala Leu Thr Ser Ser Val Thr His Leu Leu Glu Leu Asn
                165                 170                 175

Pro Leu Arg Glu Leu Val Thr Met Gly Glu Asn Leu Gln Val Arg Val
            180                 185                 190

Glu Arg Arg Ala Ala Leu Val Asn Ser Trp Tyr Glu Leu Phe Pro Arg
        195                 200                 205

Ser Thr Gly Gly Trp Asp Glu Ser Gly Thr Pro Val His Gly Thr Phe
    210                 215                 220

Ala Thr Thr Ala Gln Ala Leu Glu Arg Val Ala Lys Met Gly Phe Asp
```

```
                225                 230                 235                 240
Thr Val Tyr Phe Pro Pro Ile His Pro Ile Gly Glu Val Asn Arg Lys
                    245                 250                 255
Gly Arg Asn Asn Thr Leu Thr Pro Glu Pro His Asp Val Gly Ser Pro
                260                 265                 270
Trp Ala Ile Gly Ser Lys Asp Gly His Asp Ala Thr His Pro Arg
            275                 280                 285
Leu Gly Thr Ile Glu Asp Phe Gln Ala Leu Leu Ala Arg Ala Arg Glu
        290                 295                 300
Leu Asn Leu Glu Val Ala Leu Asp Leu Ala Leu Gln Ala Ala Pro Asp
305                 310                 315                 320
His Pro Trp Ala Gln Glu His Arg Glu Phe Phe Thr Val Leu Ala Asp
                325                 330                 335
Gly Thr Ile Ala Tyr Ala Glu Asn Pro Pro Lys Lys Tyr Gln Asp Ile
            340                 345                 350
Tyr Pro Ile Asn Phe Asp Asn Ala Ala Pro Arg Ile Tyr Glu Glu Val
        355                 360                 365
Tyr Arg Val Val Lys Phe Trp Val Asp Leu Gly Val Thr Thr Phe Arg
    370                 375                 380
Val Asp Asn Pro His Thr Lys Pro Ala Asn Phe Trp Gln Trp Leu Ile
385                 390                 395                 400
Ser Ala Ile His Lys Ser Asn Pro Glu Val Ile Phe Leu Ala Glu Ala
                405                 410                 415
Phe Thr Arg Pro Ala Arg Leu Tyr Gly Leu Ala Lys Ile Gly Phe Ser
            420                 425                 430
Gln Ser Tyr Thr Tyr Phe Thr Trp Lys Val Thr Lys Glu Glu Leu Thr
        435                 440                 445
Glu Phe Ala Thr Glu Ile Ala Arg Met Ala Asp Ile Ser Arg Pro Asn
    450                 455                 460
Leu Phe Val Asn Thr Pro Asp Ile Leu His Ala Ser Leu Gln His Gly
465                 470                 475                 480
Gly Arg Ala Met Phe Ala Ile Arg Ala Ala Leu Ala Ala Thr Met Ser
                485                 490                 495
Pro Val Trp Gly Val Tyr Ser Gly Tyr Glu Leu Phe Glu His Glu Ala
                500                 505                 510
Val Lys Pro Gly Ser Glu Glu Tyr Leu Asp Ser Glu Lys Tyr Glu Leu
            515                 520                 525
Arg Pro Arg Asp Phe Lys Gly Ala Leu Glu Arg Gly Asp Ser Leu Glu
        530                 535                 540
Asp Tyr Ile Ala Leu Leu Asn Gln Ile Arg Arg Ala Asn Pro Ala Leu
545                 550                 555                 560
Gln Gln Leu Arg Asn Ile His Phe His Glu Ala Asp Asn Asp Gln Ile
                565                 570                 575
Ile Ala Tyr Ser Lys Val Asp Ala Leu Thr Gly Asn Thr Val Leu Ile
            580                 585                 590
Val Val Asn Leu Asp Pro Arg Ser Ala Arg Glu Ala Thr Val Arg Leu
        595                 600                 605
Asp Leu Gly Ala Leu Gly Leu Glu Ala Gly Ala Gln Phe Glu Val Arg
    610                 615                 620
Asp Ala Ile Thr Asp Ser Arg Tyr Leu Trp Ser Glu Thr Asn Phe Val
625                 630                 635                 640
Arg Leu Glu Pro Leu Arg Asp Val Ala His Ile Phe Val Leu Pro Glu
                645                 650                 655
```

Leu Pro Ala Ser Arg Arg Glu Arg Leu Ala Trp Arg Glu Ile Lys Thr
            660                 665                 670

Tyr Arg Ala
        675

<210> SEQ ID NO 3
<211> LENGTH: 23
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 3
gayggnaayc cngcnaargc ngt                                              23

<210> SEQ ID NO 4
<211> LENGTH: 23
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 4
gcngtngtng gngarathgt ncc                                              23

<210> SEQ ID NO 5
<211> LENGTH: 30
<212> TYPE: DNA
<213> ORGANISM: Artificial sequence
<220> FEATURE:
<223> OTHER INFORMATION: Synthetic DNA

<400> SEQUENCE: 5
tgaataggct cagccgccac tgaagaatcc                                       30

-continued

<210> SEQ ID NO 6
<211> LENGTH: 28
<212> TYPE: DNA
<213> ORGANISM: Artificial sequence
<220> FEATURE:
<223> OTHER INFORMATION: Synthetic DNA

<400> SEQUENCE: 6
tcagatcatc gcctactcca aggttgat                                              28

<210> SEQ ID NO 7
<211> LENGTH: 24
<212> TYPE: DNA
<213> ORGANISM: Artificial sequence
<220> FEATURE:
<223> OTHER INFORMATION: Synthetic DNA

<400> SEQUENCE: 7
acgccacaca atagccgaga cagg                                                  24

<210> SEQ ID NO 8
<211> LENGTH: 30
<212> TYPE: DNA
<213> ORGANISM: Artificial sequence
<220> FEATURE:
<223> OTHER INFORMATION: Synthetic DNA

<400> SEQUENCE: 8
ctgtggtcag agacgaactt tgtccgcctc                                            30

<210> SEQ ID NO 9
<211> LENGTH: 27
<212> TYPE: DNA
<213> ORGANISM: Artificial sequence
<220> FEATURE:
<223> OTHER INFORMATION: Synthetic DNA

<400> SEQUENCE: 9
ggagagattc gtcattgagt tcactcg                                               27

<210> SEQ ID NO 10
<211> LENGTH: 26
<212> TYPE: DNA
<213> ORGANISM: Artificial sequence
<220> FEATURE:
<223> OTHER INFORMATION: Synthetic DNA

<400> SEQUENCE: 10
tcagcccgct cgcggtgacc taagtc                                                26

<210> SEQ ID NO 11
<211> LENGTH: 11
<212> TYPE: PRT
<213> ORGANISM: Artificial sequence
<220> FEATURE:
<223> OTHER INFORMATION: Conserved Internal Peptide Sequence
<220> FEATURE:
<221> NAME/KEY: MISC_FEATURE
<222> LOCATION: (7)..(7)
<223> OTHER INFORMATION: Xaa = Lys or Arg
<220> FEATURE:
<221> NAME/KEY: MISC_FEATURE
<222> LOCATION: (9)..(9)
<223> OTHER INFORMATION: Xaa = Gln or Glu

<400> SEQUENCE: 11

Ala Glu Asn Pro Pro Lys Xaa Tyr Xaa Asp Ile

```
1               5               10

<210> SEQ ID NO 12
<211> LENGTH: 10
<212> TYPE: PRT
<213> ORGANISM: Artificial sequence
<220> FEATURE:
<223> OTHER INFORMATION: Conserved Internal Peptide Sequence
<220> FEATURE:
<221> NAME/KEY: MISC_FEATURE
<222> LOCATION: (3)..(3)
<223> OTHER INFORMATION: Xaa = Val or Ile

<400> SEQUENCE: 12

Phe Arg Xaa Asp Asn Pro His Thr Lys Pro
1               5               10
```